United States Patent
Araki et al.

(10) Patent No.: US 9,278,941 B2
(45) Date of Patent: *Mar. 8, 2016

(54) AZOLE DERIVATIVE AND USES THEREOF

(71) Applicant: Kureha Corporation, Tokyo (JP)

(72) Inventors: Nobuyuki Araki, Tokyo (JP); Taiji Miyake, Tokyo (JP); Emiko Obata, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/359,449

(22) PCT Filed: Nov. 16, 2012

(86) PCT No.: PCT/JP2012/079778
§ 371 (c)(1),
(2) Date: May 20, 2014

(87) PCT Pub. No.: WO2013/077265
PCT Pub. Date: May 30, 2013

(65) Prior Publication Data
US 2014/0315967 A1    Oct. 23, 2014

(30) Foreign Application Priority Data

Nov. 25, 2011  (JP) ................................ 2011-258223
Nov. 25, 2011  (JP) ................................ 2011-258231

(51) Int. Cl.
*A01N 43/653*   (2006.01)
*C07D 249/08*   (2006.01)
*A01N 43/50*    (2006.01)

(52) U.S. Cl.
CPC .............. *C07D 249/08* (2013.01); *A01N 43/50* (2013.01); *A01N 43/653* (2013.01)

(58) Field of Classification Search
None
See application file for complete search history.

(56) References Cited

U.S. PATENT DOCUMENTS

| | | |
|---|---|---|
| 4,503,063 A | 3/1985 | Richardson et al. |
| 4,547,214 A | 10/1985 | Crowley et al. |
| 4,904,682 A | 2/1990 | Kramer et al. |
| 4,938,792 A | 7/1990 | Kumazawa et al. |
| 5,028,254 A | 7/1991 | Kumazawa et al. |
| 5,047,548 A | 9/1991 | Richardson et al. |
| 5,159,118 A | 10/1992 | Kumazawa et al. |
| 5,239,089 A | 8/1993 | Kumazawa et al. |
| 5,256,683 A | 10/1993 | Hutt et al. |
| 5,292,764 A | 3/1994 | Arahira et al. |
| 5,380,743 A | 1/1995 | Hutt et al. |
| 5,414,105 A | 5/1995 | Kumazawa et al. |
| 5,639,918 A | 6/1997 | Hutt et al. |
| 2011/0124877 A1 | 5/2011 | Ito et al. |
| 2014/0179517 A1 | 6/2014 | Araki et al. |

FOREIGN PATENT DOCUMENTS

| | | |
|---|---|---|
| CN | 1044814 A | 8/1990 |
| CN | 103562187 A | 2/2014 |
| DE | 39 02 031 A1 | 7/1990 |
| DE | 4320498 A1 | 12/1994 |
| EP | 004633 A1 | 3/1982 |
| EP | 0086917 A1 | 8/1983 |
| EP | 0 267 778 A2 | 5/1988 |
| EP | 0106515 B1 | 12/1988 |
| EP | 0 313 983 A2 | 5/1989 |
| EP | 0341954 A1 | 11/1989 |
| EP | 0 488 348 A1 | 6/1992 |
| EP | 0 329 397 B1 | 10/1993 |
| IL | 85428 A | 12/1992 |
| JP | 58-134079 A | 8/1983 |
| JP | 59-82376 A | 5/1984 |
| JP | 1-93574 A | 4/1989 |
| JP | 01149776 A | 6/1989 |
| JP | 01186871 A | 7/1989 |
| JP | 01186871 A1 | 7/1989 |
| JP | 1-301664 A | 12/1989 |
| JP | 2-42003 A | 2/1990 |
| JP | 04202190 A | 7/1992 |
| JP | 5-271197 A | 10/1993 |
| WO | 2009/088070 A1 | 7/2009 |
| WO | 2009088070 A1 | 7/2009 |
| WO | 2010-023862 A1 | 3/2010 |
| WO | 2010023862 A1 | 3/2010 |
| WO | 2010/074021 A1 | 7/2010 |
| WO | 2010074021 A1 | 7/2010 |
| WO | WO 2011/070771 A1 | 6/2011 |

OTHER PUBLICATIONS

Chinese Office Action and Search Report dated Jan. 23, 2015, for Chinese Application No. 201280056290.0 with the English translation.
Extended European Search Report issued Jun. 17, 2015, in European Patent Application No. 12851782.8.
English translation of International Preliminary Report on Patentability and Written Opinion issued Jun. 19, 2014, in PCT International Application No. PCT/JP2012/079778.
International Search Report of PCT/JP2012/079778 dated Dec. 11, 2012.
Second Office Action issued Jul. 16, 2015, in Chinese Patent Application No. 201280056290.0, with English translation.
Extended European Search Report for European Application No. 12797440.0 dated Nov. 19, 2014.
International Search Report, issued in PCT/JP2012/064534, dated Jul. 31, 2012.
Japanese Reasons for Refusal for Application No. 2013-545903, dated Nov. 17, 2015 with English language translation.

*Primary Examiner* — Alicia L Otton
(74) *Attorney, Agent, or Firm* — Birch, Stewart, Kolasch & Birch, LLP

(57) ABSTRACT

In order to provide a compound which exhibits a high controlling effect against plant diseases and is able to reduce phytotoxicity, the present invention is a triazole derivative represented by General Formula (I), the azole derivative being a (−)-enantiomer or (+)-enantiomer having an —$R^1$ group, hydroxy group, and substituted or unsubstituted benzyl group bonded to a cyclopentane ring in cis-form.

14 Claims, No Drawings

AZOLE DERIVATIVE AND USES THEREOF

TECHNICAL FIELD

The present invention relates to an enantiomer of an azole derivative and to an agricultural and horticultural agent or industrial material protecting agent containing this.

BACKGROUND ART

A certain type of 2-substitutable-5-benzyl-1-azolylmethyl cyclopentanol derivative is known to have a fungicidal effect (see, for example Patent Document 1 and Patent Document 2).

PRIOR ART DOCUMENTS

Patent Documents

Patent Document 1
Japanese Laid-open Patent Publication No. JP01-93574A (Apr. 12, 1989).
Patent Document 2
Japanese Laid-open Patent Publication No. JP01-186871A (Jul. 26, 1989)

SUMMARY OF THE INVENTION

Problem Solved by the Invention

There is demand for an agricultural and horticultural agent that is non-toxic to humans, safe to handle, and has a controlling effect on a wide variety of plant diseases.

It is an object of the present invention to solve this problem by providing a novel compound with a superior controlling effect that can be used as the active ingredient in agricultural and horticultural agents.

Means of Solving the Problem

The present inventors conducted extensive research to solve this problem. As a result, they discovered that an azole derivative expressed by General Formula (I) below has an excellent effect, and that each enantiomer has an even better effect. The present invention incorporates these novel discoveries.

A first aspect of the present invention is an azole derivative represented by General Formula (I) below, Formula 1

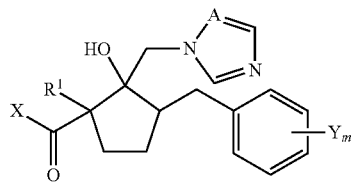

(I)

In General Formula (I), $R^1$ represents an alkyl group having 1 to 6 carbon atoms, X represents $—OR^2$ or $—NR^2R^3$, $R^2$ and $R^3$ represent a hydrogen atom, an alkyl group having 1 to 3 carbon atoms, an alkenyl group having 2 to 3 carbon atoms, or an alkynyl group having 2 to 3 carbon atoms, $R^2$ and $R^3$ being the same or different, Y represents a halogen atom, an alkyl group having 1 to 4 carbon atoms, a haloalkyl group having 1 to 4 carbon atoms, an alkoxy group having 1 to 4 carbon atoms or a haloalkoxy group having 1 to 4 carbon atoms, m represents an integer from 0 to 5, and A represents a nitrogen atom or a methine group; in which the azole derivative is a (−)-enantiomer having an $—R^1$ group, hydroxy group, and substituted or unsubstituted benzyl group bonded to a cyclopentane ring in cis-form.

A second aspect of the present invention is an azole derivative represented by General Formula (I) above, in which the azole derivative is a (+)-enantiomer having an $—R^1$ group, hydroxy group, and substituted or unsubstituted benzyl group bonded to a cyclopentane ring in cis-form.

An industrial material protecting agent or agricultural and horticultural agent of the present invention contains as an active ingredient either one of the azole derivatives described above.

A method for controlling a plant disease according to the present invention includes a foliar treatment or non-foliar treatment step using the agricultural and horticultural agent described above.

Effect of the Invention

The azole derivatives of the present invention have a superior antifungal effect on many fungi that cause plant diseases. Therefore, agents containing an azole derivative of the present invention as an active ingredient can exert a superior controlling effect on a wide variety of plant diseases.

BEST MODE FOR CARRYING OUT THE INVENTION

The following is an explanation of an azole derivative of the present invention.
1. Azole Derivative
A first aspect of the present invention is an azole derivative represented by General Formula (I) below, Formula 2

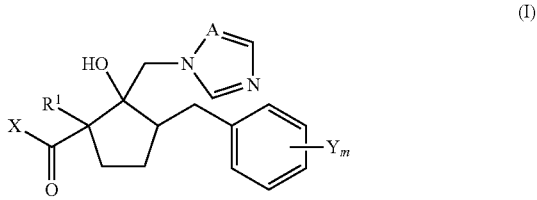

(I)

In General Formula (I), $R^1$ represents an alkyl group having 1 to 6 carbon atoms, X represents $—OR^2$ or $—NR^2R^3$, $R^2$ and $R^3$ represent a hydrogen atom, an alkyl group having 1 to 3 carbon atoms, an alkenyl group having 2 to 3 carbon atoms, or an alkynyl group having 2 to 3 carbon atoms, $R^2$ and $R^3$ being the same or different, Y represents a halogen atom, an alkyl group having 1 to 4 carbon atoms, a haloalkyl group having 1 to 4 carbon atoms, an alkoxy group having 1 to 4 carbon atoms or a haloalkoxy group having 1 to 4 carbon atoms, m represents an integer from 0 to 5, and A represents a nitrogen atom or a methine group; in which the azole derivative is a (−)-enantiomer having an $—R^1$ group, hydroxy group, and substituted or unsubstituted benzyl group bonded to a cyclopentane ring in cis-form.

A second aspect of the present invention is an azole derivative represented by General Formula (I) above, in which the azole derivative is a (+)-enantiomer having an —$R^1$ group, hydroxy group, and substituted or unsubstituted benzyl group bonded to a cyclopentane ring in cis-form.

$R^1$ represents an alkyl group with 1 to 6 carbon atoms. Examples of alkyl groups with 1 to 6 carbon atoms include a methyl group, ethyl group, (1-methyl)ethyl group, n-propyl group, 1-methyl propyl group, 2-methyl propyl group, n-butyl group, 1-methylbutyl group, 2-methylbutyl group, 1-ethyl propyl group and 1,1-dimethyl ethyl group. The present invention is not limited to these examples. Among these, an alkyl group with 1 to 4 carbon atoms is preferred, and a methyl group and ethyl group are especially preferred.

X represents —$OR^2$ or —$NR^2R^3$. $R^2$ and $R^3$ represent a hydrogen atom, an alkyl group having 1 to 3 carbon atoms, an alkenyl group having 2 to 3 carbon atoms, or an alkynyl group having 2 to 3 carbon atoms. $R^2$ and $R^3$ in —$NR^2R^3$ can be the same or different.

Examples of —$OR^2$ include a hydroxy group, methoxy group, ethoxy group, propoxy group, isopropoxy, allyloxy group, and propargyl group.

Examples of —$NR^2R^3$ include an amino group, methylamino group, dimethylamino group, ethyl methyl amino group, methyl propyl amino group, ethylamino group, diethylamino group, ethyl propyl amino group, and dipropyl amino group.

X is preferably —$OR^2$. Among these, a hydroxy group, methoxy group, ethoxy group or propoxy group is preferred, and a methoxy group is especially preferred.

Y represents a halogen atom, an alkyl group having 1 to 4 carbon atoms, a haloalkyl group having 1 to 4 carbon atoms, an alkoxy group having 1 to 4 carbon atoms, or a haloalkoxy group having 1 to 4 carbon atoms.

Specific examples of halogen atoms include chlorine atoms, fluorine atoms, bromine atoms and iodine atoms.

Examples of alkyl groups having 1 to 4 carbon atoms include a methyl group, ethyl group, n-propyl group, 1-methyl ethyl group, 2-methyl propyl group, n-butyl group, and 1,1-dimethyl ethyl group.

Examples of haloalkyl groups having 1 to 4 carbon atoms include a trifluoromethyl group, pentafluoroethyl group, chloromethyl group, trichloromethyl group, and bromomethyl group.

Examples of alkoxy groups having 1 to 4 carbon atoms include a methoxy group, ethoxy group, and n-propoxy group.

Examples of haloalkoxy groups having 1 to 4 carbon atoms include a trifluoromethoxy group, difluoromethoxy group, pentafluoroethoxy group, and 2,2,2-trifluoro ethoxy group.

Y is preferably a halogen atom. Among these, a fluorine atom and a chlorine atom are preferred, and a chlorine atom is especially preferred.

Here, m represents an integer from 0 to 5. When m is equal to or greater than 2, Y can be the same or different. Preferably, m is 0 or 1. Between these, 1 is especially preferred. When m is 1, Y is not limited to a bonding position but 4-substitutable benzyl is preferred.

A represents a nitrogen atom or a methine group. Between these, a nitrogen atom is preferred.

An azole derivative represented by General Formula (I) according to the present invention is a compound having an —$R^1$ group, hydroxy group, and substituted or unsubstituted benzyl group bonded to a cyclopentane ring in cis-form. This compound is referred to below as azole derivative (I). The compound having an —$R^1$ group, hydroxy group, and substituted or unsubstituted benzyl group bonded to a cyclopentane ring in cis-form exists in the form of a pair of enantiomers. The azole derivative in the first aspect of the present invention is a (–)-enantiomer. This enantiomer is referred to below as azole derivative (I(–)). The azole derivative in the second aspect of the present invention is a (+)-enantiomer, which is the other enantiomer in the pair. This enantiomer is referred to below as azole derivative (I(+)). In the present specification, the (–)-enantiomer is the enantiomer whose plane-polarized light along the D-line of a sodium lamp is rotated to the left, and the (+)-enantiomer is the enantiomer whose plane-polarized light along the D-line of a sodium lamp is rotated to the right. Unless otherwise indicated, the enantiomers of the azole derivative (I)—azole derivative (I(–)) and azole derivative (I(+))—are represented in racemic form in the present specification.

In the present specification, the carbon atom bonded to the —$R^1$ group, the carbon atom bonded to the hydroxy group, and the carbon atom bonded to the substituted or unsubstituted benzyl group in the cyclopentane ring, are in the 1-position, the 2-position and the 3-position of the cyclopentane ring, respectively. In the specification, "1,2-cis" and "1,3-cis" refer to the —$R^1$ group in the 1-position, the hydroxy group in the 2-position, and the substituted or unsubstituted benzyl group in the 3-position of the cyclopentane ring in the azole derivative represented by General Formula (I), or to the functional groups corresponding to these in an intermediate compound of the azole derivative.

A preferred example of an azole derivative (I(–)) is an azole derivative represented by General Formula (Ia) below, Formula 3

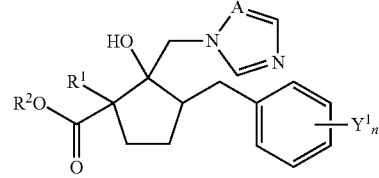

(Ia)

In General Formula (Ia), $R^1$, $R^2$ and A are the same as $R^1$, $R^2$ and A in General Formula (I), $Y^1$ represents a halogen atom, and n represents 0 or 1; in which the azole derivative is a (–)-enantiomer having an —$R^1$ group, hydroxy group, and substituted or unsubstituted benzyl group bonded to a cyclopentane ring in cis-form.

A preferred example of an azole derivative (I(+)) is an azole derivative represented by General Formula (Ia) above, in which the azole derivative is a (+)-enantiomer having an —$R^1$ group, hydroxy group, and substituted or unsubstituted benzyl group bonded to a cyclopentane ring in cis-form.

More preferred examples of azole derivatives (I(–)) include azole derivatives (I(–)) represented by General Formula (Ia) in which $R^1$ in the azole derivative (I(–)) is an alkyl group with 1 to 4 carbon atoms.

Similarly, more preferred examples of azole derivatives (I(+)) include azole derivatives (I(+)) represented by General Formula (Ia) in which $R^1$ in the azole derivative (I(+)) is an alkyl group with 1 to 4 carbon atoms.

Especially preferred examples of azole derivatives (I(–)) include azole derivatives (I(–)) represented by General Formula (Ia) in which A in the azole derivative (I(–)) is a nitrogen atom.

Similarly, especially preferred examples of azole derivatives (I(+)) include azole derivatives (I(+)) represented by General Formula (Ia) in which A in the azole derivative (I(+)) is a nitrogen atom.

Especially preferred examples of azole derivatives (I(−)) include azole derivatives (I(−)) represented by General Formula (Ia) in which $R^2$ in the azole derivative (I(−)) is a hydrogen atom or an alkyl group with 1 to 3 carbon atoms.

Similarly, especially of azole derivatives (I(+)) include azole derivatives (I(+)) represented by General Formula (Ia) in which $R^2$ in the azole derivative (I(+)) is a hydrogen atom or an alkyl group with 1 to 3 carbon atoms.

2. Manufacturing Method for Azole Derivatives

Enantiomer Separation

Both azole derivative (I(−)) and azole derivative (I(+)) can be preparatively separated from the racemic form of the azole derivative (I).

For example, chiral chromatography can be used to separate each of the enantiomers. More specifically, amylose tris (3,5-dimethyl phenyl carbamate), cellulose tris (3,5-dimethyl phenyl carbamate), cellulose tris (3,5-dichlorophenyl carbamate), amylose tris [(S)-α-methyl benzyl carbamate], cellulose tris (4-methyl benzoate), amylose tris (5-chloro-2-methyl phenyl carbamate) or cellulose tris (3-chloro-4-methyl phenyl carbamate) is immobilized on a silica gel carrier in the stationary phase, and hexane/ethanol (100/0-0/100), hexane/isopropanol (100/0-0/100), ethanol, methanol or acetonitrile is used as the mobile phase to separate azole derivative (I(−)) or azole derivative (I(+)) from the azole derivative (I).

The optical rotation of each preparatively separated enantiomer may be determined using any method common in the art.

Alternatively, the enantiomers can be preparatively separated from the azole derivative (I) using optically active camphorsulfonic acid as described in Japanese Laid-open Patent Publication No. 7-2802.

Manufacture of Azole Derivative (I)

There are no particular restrictions on the method used to manufacture the azole derivative (I). However, it can be manufactured by following the steps shown in Reaction Scheme 1 using as the starting material an azole derivative represented by General Formula (III) in which an —$R^1$ group, hydroxy group, and substituted or unsubstituted benzyl group are bonded to a cyclopentane ring in cis-form (referred to below as azole derivative (III)). Among the azole derivatives (I), the reactions performed in Reaction Scheme 1 can be used to manufacture an azole derivative in which X in Formula (I) is —$OR^2$ (referred to below as azole derivative (Ib)).

(Reaction Scheme 1)

Formula 4

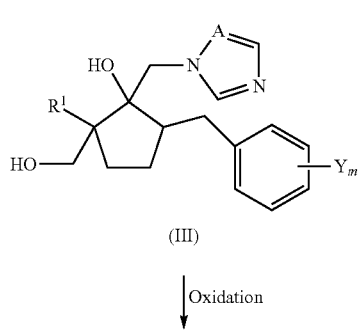

(III)

↓ Oxidation

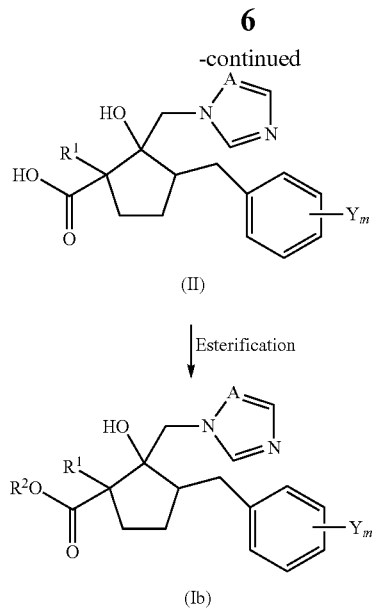

Azole derivative (III) may be a compound manufactured using a method common in the art (such as the method disclosed in International Patent Publication No. WO2011/070771).

The following is an explanation of each step in Reaction Scheme 1.

Oxidation Step

In the oxidation step, azole derivative (III) is oxidized to obtain an azole derivative represented by General Formula (II) in which an —$R^1$ group, hydroxy group, and substituted or unsubstituted benzyl group are bonded to a cyclopentane ring in cis-form (referred to below as azole derivative (II)).

There are no particular restrictions on the oxidation method that is used. A Jones reagent (chromic acid-sulfuric acid), nichrome salt, pyridinium chlorochromate, pyridinium dichloro-chromate, or potassium permanganate salt can be used as the oxidant. Among these, use of a Jones reagent is preferred.

The amount of oxidant used is from 0.3 to 20 times, and preferably from 0.5 to 10 times, the amount of azole derivative (III) in terms of the molar ratio.

The solvent depends on the type of oxidant. When a Jones reagent is used as the oxidant, a mixed solvent of acetone and water is preferred.

The reaction temperature is from −20° C. to 250° C., and preferably from −10° C. to 100° C. The reaction time is from 0.1 hours to several days, and preferably from 0.5 hours to two days.

Esterification Step

In the esterification step, the azole derivative (II) is esterified to obtain azole derivative (Ib).

There are no particular restrictions on the method used to esterify the azole derivative (II). Preferred examples include: (a) reacting it with diazomethane or a derivative thereof, or (b) reacting it with an alcohol represented by $R^2OH$ after reacting it with an azodicarboxylate derivative or phosphine compound.

First, method (a) will be explained.

An azole derivative (Ib) can be obtained by performing the reaction in an alcohol-based solvent using diazomethane or trimethylsilyl diazomethane (TMS diazomethane) as a reagent. The use of TMS diazomethane as the reagent is preferred.

The amount of reagent such as TMS diazomethane that is used is from 0.5 to 20 times, and preferably from 0.8 to 10 times, the amount of azole derivative (II).

The reaction temperature and the reaction time depend on the reagent that is used. The reaction temperature is from −20° C. to 200° C., and preferably from −10° C. to 150° C. The reaction time is from 0.1 hours to several days, and preferably from 0.5 hours to two days.

Next, method (b) will be explained. In method (b), azole derivative (Ib) is obtained using an esterification agent. In other words, in method (b), azole derivative (Ib) is obtained by allowing an azodicarboxylate such as diethyl azodicarboxylate (DEAD) or diisopropyl azodicarboxylate (DIAD) and a phosphorus compound such as tributylphosphine and triphenylphosphine to act on azole derivative (II), and then conduct a reaction with an alcohol represented by $R^2OH$. A combination of DEAD and triphenylphosphine is preferred as the esterification agent.

There are no particular restrictions on the solvent that is used. Examples include tetrahydrofuran (THF), diethyl ether, toluene and chloroform. Another solvent does not have to be used. The reaction can simply be performed using a suitable amount of alcohol represented by $R^2OH$ as the reaction reagent.

The amount of alcohol used depends on the reagent and the solvent. The amount of alcohol used is from 0.5 to 100 times, and preferably from 0.8 to 5 times, the amount of azole derivative (II).

The reaction temperature and the reaction time depend on the reagent that is used. The reaction temperature is from −20° C. to 200° C., and preferably from −10° C. to 150° C. The reaction time is from 0.1 hours to several days, and preferably from 0.5 hours to two days.

Among azole derivatives (I), an azole derivative in which X in Formula (I) is —$NR^2R^3$ (referred to below as azole derivative (Ic)) can be obtained from azole derivative (II) by performing the reaction shown in Reaction Scheme 2. More specifically, azole derivative (II) and an amine derivative represented by $NHR^2R^3$ are condensed to obtain an azole derivative represented by General Formula (Ic) (azole derivative (Ic)).

(Reaction Scheme 2)

Formula 5

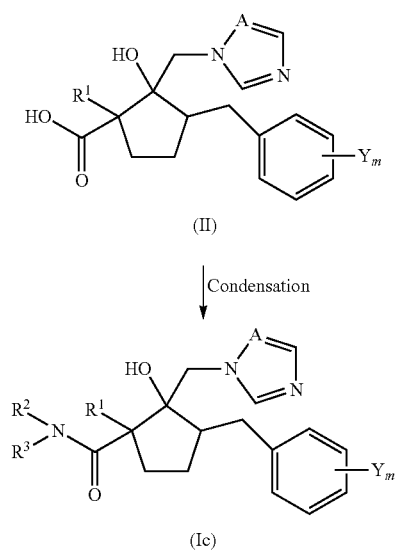

There are no specific restrictions on the condensation method. For example, dicyclohexylcarbodiimide, 1-ethyl-3-(3-dimethylaminopropyl) carbodiimide (referred to as WSC below), and diphenyl phosphate azide may be used as condensing agents. At this time, hydroxybenzotriazole and dimethylaminopyridine may be used as catalysts.

The amount of condensing agent added may be from 0.5 to 20 times, and preferably 0.8 to 10 times, the azole derivative (II) in terms of the molar ratio.

The amount of amine compound added may be from 1 to 20 times, and preferably 1.5 to 10 times, the azole derivative (II) in terms of the molar ratio.

The solvent can be selected based on the type of condensing agent that is used. For example, THF and methylene chloride may be used.

The reaction temperature and the reaction time depend on the type of reagent that is used. The reaction temperature is from −20° C. to 200° C., and preferably from −10° C. to 150° C. The reaction time is from 0.1 hours to several days, and preferably from 0.5 hours to two days.

In the method explained above, an azole derivative (I) was synthesized using an azole derivative having an —$R^1$ group, hydroxy group, and substituted or unsubstituted benzyl group bonded to a cyclopentane ring in cis-form as the starting material (azole derivative (III)). However, the method used to manufacture the azole derivative (I) is not limited to this. An azole derivative (I) can be synthesized using an azole derivative expressed by General Formula (III) having an —$R^1$ group, hydroxy group, and substituted or unsubstituted benzyl group bonded to a cyclopentane ring in trans-form as the starting material.

3. Agricultural and Horticultural Formulation—Industrial Material Protection Agent The following is an explanation of the effectiveness of agricultural and horticultural agents and industrial material protecting agents containing azole derivative (I(−)) or azole derivative (I(+)) as the active ingredient.

(1) Plant Disease Controlling Effect

Agricultural and horticultural agents containing azole derivative (I(−)) or azole derivative (I(+)) as the active ingredient have a controlling effect on a wide range of plant diseases. These plant diseases include the following:

*Phakopsora pachyrhizi, Phakopsora meibomiae, Pyricularia grisea, Cochliobolus miyabeanus, Xanthomonas oryzae, Rhizoctonia solani, Helminthosporium sigmoideum, Gibberella fujikuroi, Pythium aphani dermatum, Podosphaera leucotricha, Venturia inaequalis, Monilinia mali, Alternaria alternata, Valsa mali, Alternaria kikuchiana, Phyllactinia pyri, Gymnosporangium asiaticum, Venturia nashicola, Uncinula necator, Plasmopara viticola, Glomerella cingulata, Erysiphe graminis* f. sp. *hordei, Puccinia graminis, Puccinia striiformis, Pyrenophora graminea, Rhynchosporium secalis, Ustilago nuda, Erysiphe gramini* sf. sp. *tritici, Puccinia recondita, Puccinia striiformis, Pseudocercosporella herpotrichoides, Fusarium graminearum, Microdochium nivale, Phaeosphaeria nodorum, Septoria tritici, Gaeumannomyces graminis, Sphaerotheca fuliginea, Colletotrichum lagenarium, Pseudoperonospora cubensis, Phytophthora capsici, Fusarium oxysporum, Erysiphe cichoracearum, Alternaria solani, Erysiphe cichoracearum, Sphaerotheca humuli, Erysiphe cichoracearum, Cercospora beticola, Ustilago maydis, Penicillium italicum, Monilinia fructicola, Botrytis cinerea,* and *Sclerotinia sclerotiorum.*

Examples of plants on which the agents are effective include wild plants, plant cultivars, plants and plant cultivars obtained via conventional breeding techniques such as crossbreeding and protoplast fusion, and genetically modified plants and plant cultivars obtained via genetic techniques. Examples of genetically modified plants and plant cultivars include herbicide-tolerant crops, pest-resistant crops incorporating insecticidal protein producing genes, disease-resistant crops incorporating genes which induce resistance to diseases, taste-improving crops, storage improving crops, and yield-improving crops. Genetically modified plant cultivars include those sold under the registered trademarks Roundup Ready, Liberty Link, Clearfield, Yieldgard, Herculex and Bollgard.

(2) Plant Growth Promoting Effect

Agricultural and horticultural agents containing azole derivative (I(−)) or azole derivative (I(+)) as the active ingredient also promote growth, boost the yield, and improve the quality of garden-variety plants and a wide range of crops. Examples include the following.

Cereals such as wheat, barley and oats, rice, rapeseed, sugar cane, corn, maize, soybeans, peas, peanuts, sugar beets, cabbage, garlic, radishes, carrots, apples, pears, citrus fruits such as tangerines, oranges and lemons, peaches, cherries, avocados, mangoes, papaya, peppers, cucumbers, melons, strawberries, tobacco, tomatoes, eggplants, and ornamental plants such as grasses, chrysanthemums and azaleas.

(3) Industrial Material Protecting Effect

Industrial material protecting agents containing azole derivative (I(−)) or azole derivative (I(+)) as the active ingredient provide superior protection to materials against a wide range of harmful microorganisms that attack industrial materials. The following are examples of these microorganisms.

Paper- and pulp-degrading microorganisms (including slime-forming bacteria) such as *Aspergillus* sp., *Trichoderma* sp., *Penicillium* sp., *Geotrichum* sp., *Chaetomium* sp., *Cadophora* sp., *Ceratostomella* sp., *Cladosporium* sp., *Corticium* sp., *Lentinus* sp., *Lenzites* sp., *Phoma* sp., *Polysticus* sp., *Pullularia* sp., *Stereum* sp., *Trichosporium* sp., *Aerobacter* sp., *Bacillus* sp., *Desulfovibrio* sp., *Pseudomonas* sp., *Flavobacterium* sp. and *Micrococcus* sp., fiber-degrading microorganisms such as *Aspergillus* sp., *Penicillium* sp., *Chaetomium* sp., *Myrothecium* sp., *Curvularia* sp., *Gliomastix* sp., *Memnoniella* sp., *Sarcopodium* sp., *Stschybotrys* sp., *Stemphylium* sp., *Zygorhynchus* sp., *bacillus* sp. and *Staphylococcus* sp., wood-degrading fungi such as *Tyromyces palustris*, *Coriolus versicolor*, *Aspergillus* sp., *Penicillium* sp., *Rhizopus* sp., *Aureobasidium* sp., *Gliocladum* sp., *Cladosporium* sp., *Chaetomium* sp. and *Trichoderma* sp., leather-degrading microorganisms such as *Aspergillus* sp., *Penicillium* sp., *Chaetomium* sp., *Cladosporium* sp., *Mucor* sp., *Paecilomyces* sp., *Pilobus* sp., *Pullularia* sp., *Trichosporon* sp. and *Tricothecium* sp., rubber- and plastic-degrading microorganisms such as *Aspergillus* sp., *Penicillium* sp., *Rhizopus* sp., *Trichoderma* sp., *Chaetomium* sp., *Myrothecium* sp., *Streptomyces* sp., *Pseudomonas* sp., *Bacillus* sp., *Micrococcus* sp., *Serratia* sp., *Margarinomyces* sp. and *Monascus* sp., paint-degrading microorganisms such as *Aspergillus* sp., *Penicillium* sp., *Cladosporium* sp., *Aureobasidium* sp., *Gliocladium* sp., *Botryodiplodia* sp., *Macrosporium* sp., *Monilia* sp., *Phoma* sp., *Pullularia* sp., *Sporotrichum* sp., *Trichoderma* sp., *bacillus* sp., *Proteus* sp., *Pseudomonas* sp. and *Serratia* sp.

(4) Formulation

Agricultural and Horticultural Agent

Agricultural and horticultural agents containing azole derivative (I(−)) or azole derivative (I(+)) as the active ingredient may also include components other than azole derivative (I(−)) or azole derivative (I(+)). For example, agricultural and horticultural agents containing azole derivative (I(−)) or azole derivative (I(+)) as the active ingredient may also include solid carriers, liquid carriers, surfactant, and other formulation auxiliaries. Agricultural and horticultural agents containing azole derivative (I(−)) or azole derivative (I(+)) as the active ingredient may take a variety of different forms, including powders, wettable powders, granules and emulsions.

Agricultural and horticultural agents may include, as the active ingredient, from 0.1 to 95 wt % azole derivative (I(−)) or azole derivative (I(+)) relative to the entire weight of the agricultural and horticultural agent. Agricultural and horticultural agents preferably include from 0.5 to 90 wt % azole derivative (I(−)) or azole derivative (I(+)), and more preferably from 2 to 80 wt %.

The following carriers, diluents and surfactant can be used as formulation auxiliaries. Examples of solid carriers include talc, kaolin, bentonite, diatomaceous earth, white carbon and clay. Examples of liquid diluents include water, xylene, toluene, chlorobenzene, cyclohexane, cyclohexanone, dimethyl sulfoxide, dimethyl formamide, and alcohols. The type of surfactant used depends in the desired effect. Examples of emulsifiers include polyoxyethylene alkyl aryl ethers and polyoxyethylene sorbitan monolaurate. Examples of dispersants include lignin sulfonate and dibutyl naphthalene sulfonate. Examples of wetting agents include alkyl sulfonate and alkyl phenyl sulfonate.

The formulations may be used unaltered or may be diluted to the desired concentration using a diluent such as water. When diluted, the concentration of azole derivative (I(−)) or azole derivative (I(+)) in the spray solution is preferably from 0.001 to 1.0%.

The amount of azole derivative (I(−)) or azole derivative (I(+)) used per hectare of agricultural or horticultural land such as in a field, paddy, orchard or greenhouse is from 20 to 5,000 g, and preferably from 50 to 2,000 g. Because the concentration or amount used depends on the formulation, period of use, method of use, location of use, and intended target, this range may be increased or decreased.

Agricultural and horticultural agents of the present invention may be combined with active ingredients other than azole derivative (I(−)) or azole derivative (I(+)) to improve the performance of the agricultural and horticultural agent. Examples include fungicides, insecticides, acaricides and herbicides.

Antifungal Substances

Acibenzolar-5-methyl, 2-phenylphenol (OPP), azaconazole, azoxystrobin, amisulbrom, aixafen, benalaxyl, benomyl, benthiavalicarb-isopropyl, bicarbonate, biphenyl, bitertanol, blasticidin-S, borax, bordo mix, boscalid, bromuconazol, bronopol, bupirimate, sec-butyrate lamin, calcium polysulfide, captafol, captan, carbendazim, carboxin, carpropamid, chinomethionat, chloroneb, chloropicrin, chlorothalonil, chlozolinate, cyazofamid, cyflufenamid, cymoxanil, cyproconazole, cyprodinil, dazomet, debacarb, dichlofluanid, diclocymet, diclomezine, dicloran, diethofencarb, difenoconazole, diflumetorim, dimethomorph, dimethoxystrobin, diniconazole, dinocap, diphenylamine, dithianon, dodemorph, dodine, edifenphos, epoxiconazole, etapoxam, ethoxyquin, etridiazole, enestroburin, famoxadone, fenamidone, fenarimol, fenbuconazole, fenfuram, fenhexamid, fenoxanil, fenpiclonil, fenpropidin, fenpropimorph, fentin, ferbam, ferimzone, fluazinam, fludioxonil, flumorph, fluoromides, fluoxastrobin, fluquinconazole, flusilazole, flusulfamide, flutolanil, flutriafol, folpet, fosetyl-aluminum, fuberidazole, furalaxyl, furametpyr, fluopicolide, fluopyram, guazatine, hexachlorobenzene, hexaconazole, hymexazol, imazalil, imibenconazole, iminoctadine, ipconazole, iprobenphos, iprodione, iprovalicarb, isoprothiolane, isopyrazam, isotianil, kasugamycin, copper preparations such as copper hydroxide, copper naphthenate, copper oxychloride, copper sulfate, copper oxide and oxine-copper, kresoxim-methyl, manco copper, mancozeb, maneb, mandipropamid, mepanipyrim, mepronil, metalaxyl, metconazole, metiram, metominostrobin, mildiomycin, myclobutanil, nitrothal-isopropyl, nuarimol, ofrace, oxadixyl, oxolinic acid, oxpoconazole, oxycarboxin, oxytetracycline, pefurazoate, oryzastrobin, penconazole, pencycuron, penthiopyrad, pyribencarb, fthalide, picoxystrobin, piperalin, polyoxins, probenazole, prochloraz, procymidone, propamocarb, propiconazole, propineb, proquinazid, prothioconazole, pyraclostrobin, pyrazophos, pyrifenox, pyrimethanil, pyroquilon, quinoxyfen, quintozene, silthiofam, simeconazole, spiroxamine, sulfur and sulfur preparations, tebuconazole, tecloftalam, tecnazen, tetraconazole, thiabendazole, thifluzamide, thiophanate-methyl, thiram, thiazinyl, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, amisulbrom, sedaxane, flutianil, polyphenal, ametocradin, dimoxystrobin, metrafenone, hydroxy isoxazole, fluxapyroxad, and methasulfocarb.

Insecticides/Acaricides/Nematicides

Abamectin, acephate, acrinathrin, alanycarb, aldicarb, allethrin, amitraz, avermectin, azadirachtin, azamethiphos, azinphos-ethyl, azinphos-methyl, azocyclotin, *Bacillus firmus, Bacillus subtilis, Bacillus twin-genesis*, bendiocarb, benfuracarb, bensultap, benzoxycarbonyl formate, bifenazate, bifenthrin, bioallethrin, bioresmethrin, bistrifluoron, buprofezin, butocarboxin, butoxycarboxin, cadusafos, carbaryl, carbofuran, carbosulfan, catap, CGA 50439, chlordine, chloretoxyphos, chlorfenapyr, chlorophenbenphos, chlorfluazuron, chloromephos, chlorpyrifos, chlorpyrifos-methyl, chromaphenolzaid, clofentezine, clothianidin, chlorantraniliprole, coumaphos, cryolite, cyanophos, cyclopronthrin, cyfluthrin, cyhalothrin, cyhexatin, cypermethrin, cyphenothrin, cyromazine, cyazypyr, cyenopyrafen, DCIP, DDT, deltamethrin, demeton-S-methyl, diafenthiuron, diazinon, dichlorophen, dichloropropene, dichlorvos, dicofol, dicrotophos, dicyclanil, diflubenzuron, dimethoate, dimethylvinfos, dinobuton, dinotefuran, emamectin, endosulfan, EPN, esfenvalerate, ethiofencarb, ethion, ethiprole, ethofenprox, ethoprophos, etoxazole, famvir, fenamiphos, fenazaquin, fenbutatin oxide, fenitrothion, fenobucarb, fenothiocarb, fenoxycarb, fenpropathrin, fenpyroximate, fenthion, fenvalerate, fipronil, flonicamid, fluacrypyrim, flucycloxuron, flucythrinate, flufenoxuron, flumethrin, fluvalinate, flubendiamide, formetanate, fosthiazate, halfenprox, furathiocarb, halohenazid, gamma-HCH, heptenophos, hexaflumuron, hexythiazox, hydramethylnon, imidacloprid, imiprothrin, indoxacarb, isoprocarb, isoxathion, lufenuron, malathion, mecarbam, metam, metamidofos, methidathion, methiocarb, methomyl, methoprene, metosurin, methoxyfenozide, metolcarb, milbemectin, monochrotophos, naled, nicotine, nitenpyram, novaluron, noviflumuron, omethoate, oxamyl, oxydemeton-methyl, parathion, pametorin, phenthoate, folate, phosalone, phosmet, phosphamidon, phoxim, pirimicarb, pyrimifos methyl, profenofos, propoxur, prothiofos, pymetrozine, pyraclofos, pyrethrin, pyridaben, pyridalyl, pyrimidifen, pyriproxyfen, pyrifluquinazon, pyriprole, quinalphos, silafluofen, spinosad, spirodiclofen, spiromesifen, spirotetramat, sulfamide, sulfotepp, SZI-121, tebufenozide, tebufenpyrad, tebupirimfos, teflubenzuron, tefluthrin, temefos, terbufos, tetrachlorvinphos, thiacloprid, thiamethoxam, thiodicarb, thiofanox, thiometon, tolfenpyrad, tralomethrin, tralopyril, triazamate, triazophos, trichlorphone, triflumuron, vamidothion, varifenal, XMC, xylylcarb, imicyafos, and lepimectin.

Plant Growth Regulators

Ancymidol, 6-benzylaminopurine, paclobutrazol, diclobutrazole, uniconazole, methylcyclopropene, mepiquat chloride, ethephon, chlormequat chloride, inabenfide, prohexadione and salts thereof, trinexapac-ethyl, jasmonic acid, brassinosteroid, gibberellin and other plant hormones.

Industrial Material Protecting Agents

An industrial material protecting agent containing azole derivative (I(−)) or azole derivative (I(+)) as an active ingredient may also include components other than azole derivative (I(−)) or azole derivative (I(+)). An industrial material protecting agent containing azole derivative (I(−)) or azole derivative (I(+)) as an active ingredient can be dissolved or dispersed in a suitable liquid carrier, or mixed with a solid carrier. If necessary, an industrial material protecting agent containing azole derivative (I(−)) or azole derivative (I(+)) as an active ingredient can also include an emulsifier, dispersant, spreading agent, penetrant, wetting agent or stabilizer. An industrial material protecting agent containing azole derivative (I(−)) or azole derivative (I(+)) as an active ingredient may take a variety of forms, including wettable powders, powders, granules, tablets, pastes, suspensions and spraying materials. An industrial material protecting agent containing azole derivative (I(−)) or azole derivative (I(+)) as an active ingredient may also include fungicides, insecticides, and degradation inhibitors.

There are no particular restrictions on the liquid carrier that is used as long as it does not react with the active ingredient. Examples of liquid carriers include water; alcohols such methyl alcohols, ethyl alcohols, ethylene glycol and cellosolve; ketones such as acetone and methylethyl ketone; ethers such as dimethyl ether, diethyl ether, dioxane and tetrahydrofuran; aromatic hydrocarbons such as benzene, toluene, xylene and methyl naphthalene; aliphatic hydrocarbons such as gasoline, kerosene, heating oil, machine oil and fuel oil; acid amides such as dimethyl formamide and N-methylpyrrolidone; halogenated hydrocarbons such as chloroform and carbon tetrachloride; esters such as acetic acid ethyl ester and glycerol esters of fatty acids; nitriles such as acetonitrile; and dimethyl sulfoxide.

Examples of solid carriers that can be used include fine powders and granules of kaolin clay, bentonite, acid clay, pyrophyllite, talc, diatomaceous earth, calcite, urea, and ammonium sulfate.

Examples of emulsifiers and dispersants include soaps, alkyl sulfonic acid, alkyl aryl sulfonic acid, dialkyl sulfosuccinate, quaternary ammonium salts, oxyalkyl amine, fatty acid esters, and polyalkylene oxide-based and anhydrosorbitol-based surfactants.

When azole derivative (I(−)) or azole derivative (I(+)) is included in a formulation as the active ingredient, the proportion depends on the type of formulation and on the intended use. However, 0.1 to 99.9 wt % relative to the entire weight of the formulation can be used. During actual use, the treatment concentration may be adjusted from 0.005 to 5 wt %, and preferably from 0.01 to 1 wt %, by adding a solvent, diluent or filler.

The agricultural and horticultural agents and the industrial material protecting agents can include any type of azole derivative (I(−)) or azole derivative (I(+)) as the active ingredient.

An agricultural and horticultural agent or an industrial material protecting agent including an azole derivative (I(−)) may simply include an azole derivative (I(−)) or may include an enantiomer of the azole derivative (I(−)), that is, azole derivative (I(+)) which is the (+)-enantiomer. However, in order to increase the effectiveness of the azole derivative (I(−)) active ingredient, the amount of azole derivative (I(+)), or (+)-enantiomer, should be less than the amount of azole derivative (I(−))((−)-enantiomer). It is preferably less than 40% of the amount of azole derivative (I(−)), and more preferably less than 20% of the amount of azole derivative (I(−)). Ideally, the agent contains no azole derivative (I(+)), or (+)-enantiomer, at all.

An agricultural and horticultural agent or an industrial material protecting agents including an azole derivative (I(+)) may simply include an azole derivative (I(+)) or may include an enantiomer of the azole derivative (I(+)), that is, azole derivative (I(−)) which is the (−)-enantiomer. However, in order to increase the effectiveness of the azole derivative (I(+)) active ingredient, the amount of azole derivative (I(−)), or (−)-enantiomer, should be less than the amount of azole derivative (I(+))((+)-enantiomer). It is preferably less than 40% of the amount of azole derivative (I(+)), and more preferably less than 20% of the amount of azole derivative (I(+)). Ideally, the agent contains no azole derivative (I(−)), or (−)-enantiomer, at all.

As explained above, azole derivative (I(−)) and azole derivative (I(+)) has a superior antifungal effect on many fungi that cause plant diseases. In other words, an agricultural and horticultural disease control agent containing azole derivative (I(−)) or azole derivative (I(+)) as the active ingredient is non-toxic to humans, safe to handle, and has a controlling effect on a wide variety of plant diseases.

Because azole derivative (I(−)) and azole derivative (I(+)) has a 1,2,4-triazolyl group or imidazolyl group, an acid addition salt or metal complex of an inorganic acid or organic acid is formed. The azole derivative (I(−)) and azole derivative (I(+)) may be used in the form of an acid addition salt or metal complex.

The following is a more detailed explanation of the embodiment of the present invention with reference to examples. The present invention is not limited to these examples. Various changes are possible in terms of the details. The present invention is also not restricted to the embodiment of the present invention described above. Various modifications are possible within the scope of the claims, and certain combinations including various disclosed technical means are included in the technical scope of the present invention. All of the documents mentioned herein are incorporated by reference.

EXAMPLES

Manufacturing Example 1

Synthesis of (1,2-cis, 1,3-cis)-3-(4-chlorobenzyl)-2-hydroxy-1-methyl-2-(1H-1,2,4-triazole-1-ylmethyl) cyclopentane carboxylic acid methyl ester (1) Synthesis of (1,2-cis, 1,3-cis)-3-(4-chlorobenzyl)-2-hydroxy-1-methyl-2-(1H-1,2,4-triazole-1-ylmethyl)-1-cyclopentane cyclopentanecarboxylic acid (Azole Derivative (II): $R^1$=methyl, A=N, m=1, Y=4-Cl)

First, 6.03 g of chromic acid was dissolved in 11.3 ml of water, and 5.2 ml of concentrated sulfuric acid was slowly instilled. Next, 1.8 ml of water was added and dissolved in the resulting salt to prepare a Jones reagent. Then, 1.44 g of (1,2-cis, 1,3-cis)-3-(4-chlorobenzyl)-2-hydroxy-1-methyl-2-(1H-1,2,4-triazole-1-ylmethyl)-1-cyclopentanemethanol (Azole Derivative (III): $R^1$=methyl, A=N, m=1, Y=4-Cl) synthesized using a method common in the art was dissolved in 45 ml of acetone, 3.3 ml of the prepared Jones reagent was added, and the solution was stirred for 1.5 hours at room temperature.

After the reaction was complete, isopropyl alcohol was added, the resulting green insoluble matter was filtered out, and the filtrate was washed with acetone. The combined filtrate and cleaning solution were neutralized using a potassium hydroxide aqueous solution, and extracted using chloroform. The organic layer was washed using saturated saline and water, and then dried using anhydrous sodium sulfate. The solvent was distilled off, and the residue was purified using silica gel chromatography (Wakogel C-300, 400 g, chloroform/methanol=10/1) to obtain a colorless solid of (1,2-cis, 1,3-cis)-3-(4-chlorobenzyl)-2-hydroxy-1-methyl-2-(1H-1,2,4-triazole-1-ylmethyl)-1-cyclopentanecarboxylic acid (Compound (2)).

Yield (Amount): 0.79 g, Yield (Rate): 52.6%

$^1$H-NMR (250 MHz, CDCl$_3$) δ=0.75 (3H, s), 1.45-1.85 (3H, m), 2.04-2.18 (1H, m), 2.28-2.45 (1H, m), 2.60-2.85 (2H, m), 4.21 (1H, d, J=14.0 Hz), 4.68 (1H, d, J=14.0 Hz), 7.13 (2H, d, J=8.6 Hz), 7.24 (2H, d, J=8.6 Hz), 8.00 (1H, s), 8.25 (1H, s).

(2) Synthesis of (1,2-cis, 1,3-cis)-3-(4-chlorobenzyl)-2-hydroxy-1-methyl-2-(1H-1,2,4-triazole-1-ylmethyl)cyclopentanecarboxylic acid methyl ester (Azole Derivative (Ib): $R^1$=methyl, $R^2$=methyl, A=N, m=1, Y=4-Cl)

Next, 0.102 g (0.292 mmol) of Compound (2) was suspended in 1.0 ml of dehydrated methanol in an argon atmosphere, and 3.6 ml of dehydrated benzene was added and dissolved. Over the course of two minutes, 0.175 ml (0.350 mmol) of a hexane solution of 2.0 M trimethylsilyl diazomethane was instilled. After heat and bubbles began to be released, the solution was stirred for two hours at room temperature. After the reaction was complete, the solvent was distilled off from the yellow, homogeneous solution under reduced pressure. The residue was separated and purified using silica gel column chromatography (Wakogel C-300: 5 g, hexane/ethyl acetate=1:1) to obtain a colorless, oily (1,2-cis, 1,3-cis)-3-(4-chlorobenzyl)-2-hydroxy-1-methyl-2-(1H-1,2,4-triazole-1-ylmethyl)cyclopentane carboxylic acid methyl ester (Compound (1)).

Yield (Amount): 0.111 g, Yield (Rate): 100%

$^1$H-NMR (400 MHz, CDCl$_3$, TMS) δ=0.70 (3H, s), 1.76-1.52 (3H, m), 2.05 (1H, m), 2.35 (1H, m), 2.66 (2H, m), 3.69 (3H, s), 4.21 (1H, d, J=14.1 Hz), 4.60 (1H, brs), 4.62 (1H, d, J=14.1 Hz), 7.10 (2H, d, J=8.5 Hz), 7.23 (2H, d, J=8.5 Hz), 8.00 (1H, s), 8.20 (1H, s)

IR (KBr) vcm$^{-1}$: 3420, 3152, 2992, 2944, 2872, 1722, 1628, 1512, 1494, 1460, 1418, 1384, 1370, 1272, 1228, 1204, 1188, 1166, 1132, 1118, 1108, 988, 976, 964, 932, 912, 878, 858, 846, 812, 794, 776, 750, 706, 676, 666, 594, 530, 486, 434, 406.

Manufacturing Example 2

Preparation of (1,2-cis, 1,3-cis)-3-(4-chlorobenzyl)-2-hydroxy-1-methyl-2-(1H-1,2,4-triazole-1-ylmethyl)cyclopentanecarboxylic acid methyl ester (−)-enantiomer and (+)-enantiomer The racemic form of Compound (1) was dissolved in ethanol, and the solution was supplied to high performance liquid chromatograph (HPLC) connected to a semi-preparative column with amylose tris (3,5-dimethyl phenyl carbamate) immobilized on silica gel carrier, and preparative separation was performed.

The specific conditions are as follows:
High-performance liquid chromatograph: LC-9A (Shimadzu Corporation)
Semi-preparative column: Daicel Chemical Industries ChiralPak IA, inner diameter: 20 mm, length: 250 mm, particle diameter: 5 m
Sample concentration: 50,000 ppm (in ethanol solution)
Mobile phase: hexane/ethanol (15:1)
Flow rate: 5 ml/min
Detection wavelength: 254 nm When separated under these conditions two peaks with different elution times were detected. The specific optical rotation of the compounds derived from the peaks was measured, and the compound eluted first was a levorotatory enantiomer ((−)-enantiomer) and the compound eluted next was a dextrorotatory enantiomer ((+)-enantiomer). The ((−)-enantiomer) is referred to as Compound (1(−)) and the ((+)-enantiomer) is referred to as Compound (1(+)) below.

The specific rotation was performed four times (Compound (1(−))) and three times (Compound (1(+))) using a Jasco P-1020 (Na lamp: 589 nm).

The specific measurement results are as follows:
Average specific optical rotation of Compound (1(−)):
$[\alpha]_{D29} = -16°$ (C=1: ethanol)
Average specific optical rotation of Compound (1(+):
$[\alpha]_{D29} = +21°$ (C=1: ethanol)

Example of Formulations

| Wettable Powder Formulation | |
|---|---|
| Compound (1(−)) or Compound (1(+)) | 50 parts |
| Lignin sulfonate | 5 parts |
| Alkyl sulfonate | 3 parts |
| Diatomaceous earth | 42 parts |

These components were pulverized and mixed together to obtain a wettable powder which was then diluted with water.

| Powder Formulation | |
|---|---|
| Compound (1(−)) or Compound (1(+)) | 3 parts |
| Clay | 40 parts |
| Talc | 57 parts |

These components were pulverized and mixed together to obtain a powder.

| Granular Formulation | |
|---|---|
| Compound (1(−)) or Compound (1(+)) | 5 parts |
| Bentonite | 43 parts |
| Clay | 45 parts |
| Lignin sulfonate | 7 parts |

These components were mixed together uniformly, kneaded while adding water, granulated using an extrusion granulator, and dried to obtain granules.

| Emulsion Formulation | |
|---|---|
| Compound (1(−)) or Compound (1(+)) | 20 parts |
| Polyoxyethylene alkyl aryl ether | 10 parts |
| Polyoxyethylene sorbitan monolaurate | 3 parts |
| Xylene | 67 parts |

These components were mixed together and dissolved to obtain an emulsion.

Test Example 1

Test of Gray Mold Disease Control Effect on Cucumbers Using Foliar Spray Treatment The wettable powder form of Compound (1(−)) or Compound (1(+)) prepared in the manner described above was diluted and suspended in water at a specific concentration (50 mg/L), and sprayed at a rate of 1,000 L/ha on cucumbers (variety: Sharp 1) in the cotyledon stage which were cultivated in square plastic pots (6 cm×6 cm). After blow drying the sprayed leaves, the plants were placed under paper disks (diameter: 8 mm) impregnated with a spore solution of *Botrytis cinerea*, and maintained under high humidity at 20° C. Four days after inoculation, the morbidity of the cucumbers to gray mold was evaluated according to the criteria shown in Table 1, and the preventative value was calculated using the following equation. The results are shown in Table 2. When the average morbidity of the sprayed plot was higher than the average morbidity of the unsprayed plot, the preventative value was 0%.

Preventative value (%)=(1−(average morbidity of the sprayed plot/average morbidity of the unsprayed plot))×100.

TABLE 1

| Morbidity | Area Ratio of Disease |
|---|---|
| 0 | No onset of disease |
| 0.5 | Area ratio of spots: <10% |
| 1 | Area ratio of spots: 10-20% |
| 2 | Area ratio of spots: 20-40% |
| 3 | Area ratio of spots: 40-60% |
| 4 | Area ratio of spots: 60-80% |
| 5 | Area ratio of spots: >80% |

TABLE 2

| | Compound | | | |
|---|---|---|---|---|
| | Compound (1(−)) | | Compound (1(+)) | |
| | Sample conc. (mg/L) | | | |
| | 50.0 | 12.5 | 50.0 | 12.5 |
| Preventative Value (%) | 100 | 64.7 | 17.6 | 0 |

Test Example 2

Test of Powdery Mildew Control Effect on Wheat Using Foliar Spray Treatment

The wettable powder form of Compound (1(−)) or Compound (1(+)) prepared in the manner described above was diluted and suspended in water at a specific concentration, and sprayed at a rate of 1,000 L/ha on wheat (variety: Agriculture and Forestry No. 61) in the second leaf stage which were cultivated in square plastic pots (6 cm×6 cm). After blow drying the sprayed leaves, the plants were sprinkled and inoculated with powdery mildew from wheat seedlings infected with powdery mildew. Seven days after inoculation, the morbidity of the wheat to powdery mildew was evaluated according to the criteria shown in Table 3, and the preventative value was calculated using the following equation.

Preventative value (%)=(1−(average morbidity of the sprayed plot/average morbidity of the unsprayed plot))×100.

TABLE 3

| Morbidity | Area Ratio of Disease |
|---|---|
| 0 | No onset of disease |
| 0.5 | Area ratio of spots: <1% |
| 1 | Area ratio of spots: 1-5% |
| 2 | Area ratio of spots: 5-10% |
| 3 | Area ratio of spots: 10-30% |
| 4 | Area ratio of spots: 30-50% |
| 5 | Area ratio of spots: >50% |

The effects are shown in Table 4.

TABLE 4

| | Compound | | | |
|---|---|---|---|---|
| | Compound (1(−)) | | Compound (1(+)) | |
| | Sample conc. (mg/L) | | | |
| | 50.0 | 12.5 | 50.0 | 12.5 |
| Preventative Value (%) | 98 | 96 | 94 | 24 |

Test Example 3

Test of Rust Control Effect on Wheat Using Foliar Spray Treatment

The wettable powder form of Compound (1(−)), Compound (1(+)) or Metconazole prepared in the manner described above was diluted and suspended in water at a specific concentration, and sprayed at a rate of 1,000 L/ha on wheat (variety: Agriculture and Forestry No. 61) in the second leaf stage which were cultivated in square plastic pots (6 cm×6 cm). After blow drying the sprayed leaves, the plants were sprayed with spores of wheat leaf rust (200 units/field, Grameen S was added to adjust the final concentration to 60 ppm), and maintained under high humidity at 25° C. for 48 hours. Afterwards, they were kept in a greenhouse. Twelve days after inoculation, the morbidity of the wheat to leaf rust was evaluated according to the criteria shown in Table 5, and the preventative value was calculated using the following equation. The results are shown in Table 6.

Preventative value (%)=(1−(average morbidity of the sprayed plot/average morbidity of the unsprayed plot))×100.

TABLE 5

| Morbidity | Peterson Rust Damage Rate Scale |
|---|---|
| 0 | No onset of disease |
| 0.5 | Area ratio of spots: <1% |
| 1 | Area ratio of spots: 1-5% |
| 2 | Area ratio of spots: 5-10% |
| 3 | Area ratio of spots: 10-30% |
| 4 | Area ratio of spots: 30-50% |
| 5 | Area ratio of spots: >50% |

TABLE 6

| | Compound | | | | | |
|---|---|---|---|---|---|---|
| | Comp. (1(−)) | | Comp. (1(+)) | | Metconazole | |
| | Sample conc. (mg/L) | | | | | |
| | 3.1 | 0.8 | 3.1 | 0.8 | 3.1 | 0.8 |
| Preventative Value (%) | 92.9 | 83.5 | 0 | 0 | 81.1 | 34.1 |

Test Example 4

Test of Brown Rust Control Effect on Wheat Using Seed Treatment

A pot test was performed to evaluate the brown rust controlling effect on wheat using seed treatment. Compound (1(−)) or Compound (1(+)) was dissolved in DMSO so the treatment amount was 20 g ai/100 kg seeds or 2 g ai/100 kg seeds, and the solution was smeared on wheat seeds in a vial, and eight wheat seeds were seeded in a 80 cm² pot. These were irrigated from below in a greenhouse. Fifteen days after seeding, the seedlings were inoculated with wheat brown rust and then kept for two days in a box. These were again irrigated from below in a greenhouse. Sixteen days after inoculation, the morbidity of the wheat to brown rust was evaluated according to the criteria shown in Table 5 for Test Example 3, and the preventative value was calculated using the following equation.

Preventative value (%)=(1−(average morbidity of the treated plot/average morbidity of the untreated plot))×100.

The results are shown in Table 7.

TABLE 7

| | Compound | | | |
|---|---|---|---|---|
| | Compound (1(−)) | | Compound (1(+)) | |
| | Amount Treated (g ai/100 kg seeds) | | | |
| | 20 | 2 | 20 | 2 |
| Preventative Value (%) | 100 | 70 | 5 | 0 |

Test Example 5

Antifungal Test for Pathogens

In this test example, an antifungal test of various pathogenic filamentous fungi was performed.

Compound (1(−)) or Compound (1(+)) was dissolved in dimethyl sulfoxide, and added to a potato-dextrose-agar (PDA) medium at 60° C. After thoroughly mixing the contents in an Erlenmeyer flask, they were poured into a Petri dish and solidified to prepare a plate medium containing Compound (1(−)) or Compound (1(+)) at a particular concentration.

Test fungi that were cultured beforehand in medium plates were punched out with a 4 mm-diameter cork borer, and inoculated in the plate media containing the agent. After inoculation, they were cultured for 1 to 14 days at the optimum growing temperature of each fungus (see the List of Cultures: 1996 Microorganisms, 10th Edition, from the Institute for Fermentation, Osaka), and the growth of the fungus was determined by the diameter of the growth. The growth rate of the fungus in the plate media containing the agent was compared to the growth rate of the fungus in the plate medium not containing the agent, and the filamentous fungi inhibition rate was determined using the following equation. In the equation, R is the filamentous fungi inhibition rate (%), dc is the diameter of the fungal growth in the untreated plate media, and dt is the diameter of the fungal growth in the treated plate media.

$$R=100(dc-dt)/dc$$

These results were evaluated using the five-level scale shown in Table 8. A higher antifungal index indicates a better antifungal effect. The results are shown in Table 9 and Table 10.

TABLE 8

| Filamentous Fungi Inhibition Rate | Antifungal Index |
|---|---|
| >90% | 5 |
| 90%-80% | 4 |
| 80%-70% | 3 |
| 70%-60% | 2 |
| <60% | 1 |

TABLE 9

| | | Compound | | | | | |
|---|---|---|---|---|---|---|---|
| | | Compound (1(−)) | | | Compound (1(+)) | | |
| | | Sample Conc. (mg/L) | | | | | |
| | | 5 | 2.5 | 1.25 | 5 | 2.5 | 1.25 |
| Antifungal Index of Each Strain | P.n | 5 | 5 | 5 | 2 | 2 | 2 |
| | P.h | 5 | 5 | 5 | 1 | 1 | 1 |
| | M.n | 5 | 5 | 3 | 1 | 1 | 1 |
| | G.g | 5 | 5 | 5 | 4 | 2 | 1 |
| | F.g | 5 | 5 | 5 | 2 | 1 | 1 |
| | U.n | 5 | 5 | 5 | 4 | 3 | 2 |
| | P.o | 5 | 5 | 4 | 5 | 2 | 1 |
| | R.s | 5 | 5 | 5 | 4 | 2 | 2 |
| | G.f | 5 | 5 | 5 | 3 | 2 | 1 |
| | R.o | 5 | 5 | 5 | 1 | 1 | 1 |
| | A.m | 5 | 4 | 3 | 3 | 2 | 1 |
| | S.s | 5 | 5 | 5 | 1 | 1 | 1 |
| | B.c | 5 | 5 | 5 | 4 | 1 | 1 |
| | G.c | 5 | 5 | 5 | 2 | 1 | 1 |
| | F.c | 5 | 5 | 5 | 4 | 3 | 2 |

TABLE 10

| | | Compound | | | | | | | |
|---|---|---|---|---|---|---|---|---|---|
| | | Compound (1(−)) | | | | Compound (1(+)) | | | |
| | | Sample Conc. (mg/L) | | | | | | | |
| | | 0.63 | 0.31 | 0.16 | 0.08 | 0.63 | 0.31 | 0.16 | 0.08 |
| Antifungal Index of Each Strain | P.g | 5 | 4 | 3 | 2 | 5 | 4 | 1 | 1 |
| | P.i | 5 | 3 | 1 | 1 | 2 | 1 | 1 | 1 |
| | C.b | 5 | 5 | 5 | 5 | 4 | 3 | 2 | 1 |
| | R.sec | 5 | 5 | 5 | 5 | 5 | 5 | 5 | 3 |

The abbreviations in Table 9 and Table 10 represent the following strains:
P.n: *Phaeosphaeria nodorum*
P.h: *Pseudocercoporella herpotrichoides*
M.n: *Microdochium nivale*
G.g: *Gaeumannomyces graminis*
F.g: *Fusarium graminearum*
U.n: *Ustilago nuda*
P.o: *Pyricularia oryzae*
R.s: *Rhizoctonia solani*
G.f: *Gibberella fujikuroi*
R.o: *Rhizopus oryzae*
A.m: *Alternaria alternata*
S.s: *Sclerotinia sclerotiorum*
B.c: *Botrytis cinerea*
G.c: *Glomerella* cingurata
F.c: *Fusarium oxysporum*
P.g: *Pyrenophora graminea*
P.i: *Penicillium italicum*
C.b: *Cercospora beticola*
R.sec: *Rhynchosporium secalis*

Test Example 6

Test of Leaf Blotch Control Effect on Wheat Using Foliar Spray Treatment

The wettable powder form of Compound (1(−)) or Compound (1(+)) prepared in the manner described above was diluted and suspended in water at a specific concentration, and sprayed at a rate of 1,000 L/ha on wheat (variety: Agriculture and Forestry No. 61) in the second leaf stage which were cultivated in square plastic pots (6 cm×6 cm). After blow drying the sprayed leaves, the plants were sprinkled and inoculated with wheat leaf blight. Thirty days after inoculation, the morbidity of the wheat to powdery mildew was evaluated according to the criteria shown in Table 3, and the preventative value was calculated using the following equation. The results are shown in Table 11. When the average morbidity of the sprayed plot was higher than the average morbidity of the unsprayed plot, the preventative value was 0%.

Preventative value (%)=(1−(average morbidity of the sprayed plot/average morbidity of the unsprayed plot))×100.

TABLE 11

| | Compound | | | | | |
|---|---|---|---|---|---|---|
| | Comp. (1(+)) | | Comp. (1(−)) | | Metconazole | |
| | Sample conc. (mg/L) | | | | | |
| | 50 | 12.5 | 50 | 12.5 | 50 | 12.5 |
| Preventative Value (%) | 77.5 | 67.5 | 65 | 37.5 | 62.5 | 0 |

Test Example 7

Phytotoxicity Evaluation of Growth Inhibition of Wheat Seeds Using Seed Treatment A pot test was used to perform a phytotoxicity evaluation of growth inhibition using a seed treatment. Compound (1(−)) or Compound (1(+)) was dissolved in DMSO so the treatment amount was 2 or 20 g ai/100 kg seeds, and the solution was smeared on wheat seeds in a vial, and eight wheat seeds were seeded in a 80 cm² pot. These were irrigated from below in a greenhouse. Fifteen days after seeding, the length of the wheat was evaluated. The results are shown in Table 12.

TABLE 12

| | Compound | | | | |
|---|---|---|---|---|---|
| | Compound (1(+)) | | Compound (1(−)) | | Untreated |
| | Amount Treated (g ai/100 kg seeds) | | | | |
| | 2 | 20 | 2 | 20 | — |
| Average Plant Length (cm) | 22 | 14 | 11 | 6 | 21 |

Test Example 8

Antifungal Test Against Wheat Leaf Blight

In this test example, an antifungal test was performed for wheat leaf blight.

Compound (1(−)), Compound (1(+)) or Metconazole was dissolved in dimethyl sulfoxide, and added to a potato-dextrose-agar (PDA) medium at 60° C. After thoroughly mixing the contents in an Erlenmeyer flask, they were poured into a Petri dish and solidified to prepare a plate medium containing Compound (1(−)), Compound (1(+)) or Metconazole at a concentration from 0.31 to 1.25 mg/L.

Wheat leaf blight (*Septoria tritici*) cultured beforehand in a medium plate was punched out with a 4 mm-diameter cork borer, and inoculated in the plate media containing the agent. After inoculation, they were cultured for 19 days at 25° C., and the growth of the fungus was determined by the diameter of the growth. The growth rate of the fungus in the plate media containing the agent was compared to the growth rate of the fungus in the plate medium not containing the agent, and the filamentous fungi inhibition rate was determined using the following equation. In the equation, R is the filamentous fungi inhibition rate (%), dc is the diameter of the fungal growth in the untreated plate media, and dt is the diameter of the fungal growth in the treated plate media.

$$R = 100(dc - dt)/dc$$

These results were evaluated using the five-level scale shown in Table 8 for Test Example 5. A higher antifungal index indicates a better antifungal effect. The results are shown in Table 13.

TABLE 13

| | Compound | | | | | | | | |
|---|---|---|---|---|---|---|---|---|---|
| | Compound (1(+)) | | | Compound (1(−)) | | | Metconazole | | |
| | Sample conc. (mg/L) | | | | | | | | |
| | 1.25 | 0.63 | 0.31 | 1.25 | 0.63 | 0.31 | 1.25 | 0.63 | 0.31 |
| Antifungal Index | 5 | 3 | 3 | 4 | 2 | 1 | 4 | 2 | 1 |

Test Example 9

Antifungal Tests on Other Pathogens

In this test example, an antifungal test was performed on various pathogenic filamentous fungi other than wheat leaf blight.

A plate medium containing Compound (1(+)) at a particular concentration (10 mg/L) was prepared in the same manner as Test Example 8.

Test fungi (wheat blight fungus, barley stripe fungus, wheat fusarium fungus, barley loose smut fungus, rice blast fungus, rice sheath blight fungus, rice bakanae fungus, apple leaf spot fungus, *Botrytis cinerea*, cucumber vine crack fungus, citrus blue mold fungus, sugar beet brown spot fungus, or barley cloud fungus) that were cultured beforehand in medium plates were punched out with a 4 mm-diameter cork borer, and inoculated in the plate media containing the agent. After inoculation, they were cultured for 1 to 14 days at the optimum growing temperature of each fungus (see the List of Cultures: 1996 Microorganisms, 10th Edition, from the Institute for Fermentation, Osaka), and the growth of the fungus was determined by the diameter of the growth. The filamentous fungi inhibition rate was determined in the same manner as Test Example 8.

The filamentous fungi inhibition rate R was 80% or more for all of the fungi.

INDUSTRIAL APPLICABILITY

The azole derivatives of the present invention can be used advantageously as an active ingredient in fungicides for agricultural and horticultural use, plant growth regulators, and industrial material protecting agents.

The invention claimed is:

1. An azole derivative represented by General Formula (I) below:

Formula 1

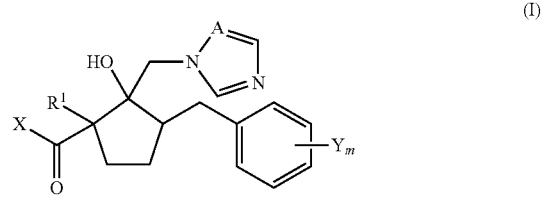

(I)

in General Formula (I), R¹ represents an alkyl group having 1 to 6 carbon atoms, X represents —OR² or —NR²R³, R² and R³ represent a hydrogen atom, an alkyl group having 1 to 3 carbon atoms, an alkenyl group having 2 to 3 carbon atoms, or an alkynyl group having 2 to 3 carbon atoms, R² and R³ being the same or different, Y represents a halogen atom, an alkyl group having 1 to 4 carbon atoms, a haloalkyl group having 1 to 4 carbon atoms, an alkoxy group having 1 to 4 carbon atoms or a haloalkoxy group having 1 to 4 carbon atoms, m represents an integer from 0 to 5, and A represents a nitrogen atom or a methine group;

the azole derivative being a (−)-enantiomer having an —R¹ group, hydroxy group, and substituted or unsubstituted benzyl group bonded to a cyclopentane ring in cis-form.

2. An azole derivative according to claim 1, wherein the azole derivative is represented by General Formula (Ia) below, Formula 2

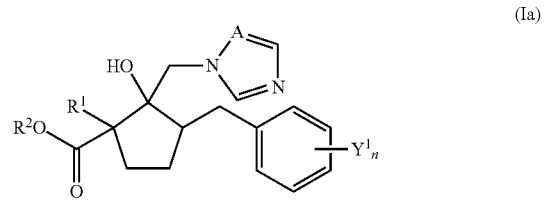

(Ia)

in General Formula (Ia), $R^1$, $R^2$ and A are the same as $R^1$, $R^2$ and A in General Formula (I), $Y^1$ represents a halogen atom, and n represents 0 or 1;

and the azole derivative is a (−)-enantiomer having an —$R^1$ group, hydroxy group, and substituted or unsubstituted benzyl group bonded to a cyclopentane ring in cis-form.

3. An azole derivative according to claim 2, wherein $R^1$ in General Formula (Ia) is an alkyl group having 1 to 4 carbon atoms.

4. An azole derivative according to claim 2, wherein A in General Formula (Ia) is a nitrogen atom.

5. An azole derivative according to claim 2, wherein $R^2$ in General Formula (Ia) is a hydrogen atom or an alkyl group having 1 to 3 carbon atoms.

6. An azole derivative represented by General Formula (I) below:

Formula 1

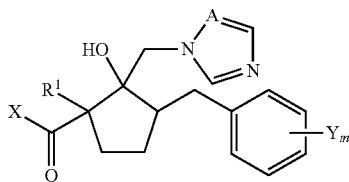

(I)

in General Formula (I), $R^1$ represents an alkyl group having 1 to 6 carbon atoms, X represents —$OR^2$ or —$NR^2R^3$, $R^2$ and $R^3$ represent a hydrogen atom, an alkyl group having 1 to 3 carbon atoms, an alkenyl group having 2 to 3 carbon atoms, or an alkynyl group having 2 to 3 carbon atoms, $R^2$ and RN being the same or different, represents a halogen atom, an alkyl group having 1 to 4 carbon atoms, a haloalkyl group having 1 to 4 carbon atoms, an alkoxy group having 1 to 4 carbon atoms or a haloalkoxy group having 1 to 4 carbon atoms, m represents an integer from 0 to 5, and A represents a nitrogen atom or a methine group;

the azole derivative being a (+)-enantiomer having an —$R^1$ group, hydroxy group, and substituted or unsubstituted benzyl group bonded to a cyclopentane ring in cis-form.

7. An azole derivative according to claim 6, wherein the azole derivative is represented by General Formula (Ia) below, Formula 2

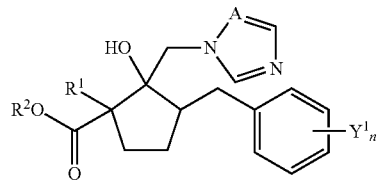

(Ia)

in General Formula (Ia), $R^1$, $R^2$ and A are the same as $R^1$, $R^2$ and A in General Formula (I), $Y^1$ represents a halogen atom, and n represents 0 or 1;

and the azole derivative is a (+)-enantiomer having an —$R^1$ group, hydroxy group, and substituted or unsubstituted benzyl group bonded to a cyclopentane ring in cis-form.

8. An azole derivative according to claim 7, wherein $R^1$ in General Formula (Ia) is an alkyl group having 1 to 4 carbon atoms.

9. An azole derivative according to claim 7, wherein A in General Formula (Ia) is a nitrogen atom.

10. An azole derivative according to claim 7, wherein $R^2$ in General Formula (Ia) is a hydrogen atom or an alkyl group having 1 to 3 carbon atoms.

11. An industrial material protecting agent or agricultural and horticultural agent containing as an active ingredient an azole derivative according claim 6.

12. A method for controlling a plant disease comprising a foliar treatment or non-foliar treatment step using an agricultural and horticultural agent according to claim 11.

13. An industrial material protecting agent or agricultural and horticultural agent containing as an active ingredient an azole derivative according to claim 1.

14. A method for controlling a plant disease comprising a foliar treatment or non-foliar treatment step using an agricultural and horticultural agent according to claim 13.

* * * * *